(12) United States Patent
Brown et al.

(10) Patent No.: US 6,825,148 B2
(45) Date of Patent: Nov. 30, 2004

(54) NICKEL-CONTAINING ETHYLENE OLIGOMERIZATION CATALYST AND USE THEREOF

(75) Inventors: David Stephen Brown, Sugar Land, TX (US); Richard Edward Robertson, Baton Rouge, LA (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/832,070

(22) Filed: Apr. 10, 2001

(65) Prior Publication Data

US 2002/0173685 A1 Nov. 21, 2002

(51) Int. Cl.⁷ .............................. B01J 31/00; C08F 4/06; C08F 4/44
(52) U.S. Cl. ..................... 502/162; 502/169; 502/170; 502/171; 526/135; 526/136; 526/172
(58) Field of Search ................................. 502/162, 169, 502/170, 171; 526/135, 136, 172

(56) References Cited

U.S. PATENT DOCUMENTS

| | | | |
|---|---|---|---|
| 3,676,523 A | | 7/1972 | Mason .............. 260/683.15 D |
| 4,970,185 A | * | 11/1990 | Sie et al. .................... 502/125 |
| 5,143,873 A | * | 9/1992 | Bryndza et al. ............ 502/162 |
| 5,286,695 A | * | 2/1994 | Hirose et al. ............... 502/117 |
| 5,929,181 A | | 7/1999 | Makovetsky et al. ....... 526/171 |

OTHER PUBLICATIONS

Aldrich Catalog, p. 1312, copyright 1990.*

CRC Handbook of Chemistry and Physics, 63d ed., copyright 1982, p. C–67.*

Liu, Dongbing et al: "Catalytic Oligomerization of Ethylene to Lower Alpha–olefins by Nickel Chelate" (Abstract); Yingyong Huaxue (1997), 14(3), 99–101.

* cited by examiner

*Primary Examiner*—Mark L. Bell
*Assistant Examiner*—J. Pasterczyk

(57) ABSTRACT

A process for the oligomerization of ethylene to a mixture of olefinic products having high linearity is provided, by using a catalyst comprising a reaction product of a simple divalent nickel salt; a boron hydride reducing agent; a water soluble base; a ligand selected from the group consisting of an o-dihydrocarbylphosphinobenzoic acid and alkali metal salts thereof; and a phosphite.

35 Claims, No Drawings

NICKEL-CONTAINING ETHYLENE OLIGOMERIZATION CATALYST AND USE THEREOF

FIELD OF THE INVENTION

This invention relates to a certain nickel-containing catalyst and a process for the oligomerization of ethylene to a mixture of olefinic products having high linearity using such catalyst.

BACKGROUND OF THE INVENTION

The production of a mixture of olefinic products which are substantially alpha-olefins and which have a high degree of linearity are known. Such olefins comprise for example, those of the $C_4$–$C_{10}$ range, useful as comonomers for LLDPE or as synthetic lubricants; those of the $C_{12}$–$C_{20}$ range, useful as detergents; and higher olefins. The lower molecular weight olefins can be converted to sulfonates or alcohols by known commercial processes. The $C_{12}$–$C_{20}$ olefins find use in the detergent-products area. Lower molecular weight alcohols can be esterified with polyhydric acids, e.g., phthalic acid to form plasticizers for polyvinylchloride.

U.S. Pat. No. 3,676,523, herein incorporated by reference, discloses the use of an ethylene oligomerization catalyst in the production of such olefinic products which comprises (1) a divalent nickel salt, (2) a boron hydride reducing agent, and (3) an o-dihydrocarbylphosphinobenzoic acid or alkali metal salt thereof.

One drawback to the use of this catalyst, however, is expense. There exists a need for a lower cost catalyst in the production of such olefinic products.

SUMMARY OF THE INVENTION

This invention relates to a process for the oligomerization of ethylene to a mixture of olefinic products having high linearity by using a catalyst comprising a simple divalent nickel salt; a boron hydride reducing agent; a water soluble base; a ligand selected from the group consisting of o-dihydrocarbyl-phosphinobenzoic acids and alkali metal salts thereof; and a trivalent (three-coordinate) phosphite.

DETAILED DESCRIPTION OF THE INVENTION

It has been found that the use of a certain ligand provides for a cost effective catalyst useful in the production of olefinic products.

Nickel Salts:

In general, any simple divalent nickel salt can be employed for preparing the catalyst composition of the invention provided the nickel salt is sufficiently soluble in the reaction medium. By the term "simple divalent" nickel salt is meant a nickel atom having a formal valence of +2 and bonded through ionic or electrovalent linkages to two singly charged anionic groups (e.g., halides) or to one doubly charged anionic group (e.g., carbonate) and not complexed with or coordinated to any other additional molecular or ionic species. Simple divalent nickel salts therefore do not encompass complex divalent nickel salts which are bonded to one or two anionic groups and additionally complexed or coordinated to neutral chelating ligands or groups such as carbon monoxide and phosphines. However, simple divalent nickel salts are meant to include nickel salts containing water of crystallization in addition to one or two anionic groups.

In most instances, a simple divalent nickel salt with a solubility in the reaction diluent or solvent employed for catalyst preparation of at least 0.001 mole per liter (0.001M) is satisfactory for use as the nickel catalyst precursor. A solubility in the reaction diluent or solvent of at least 0.01 mole per liter (0.01M) is preferred, and a solubility of at least 0.05 mole per liter (0.05M) is most preferred. Reaction diluents and solvents suitably employed for catalyst preparation are the polar organic solvents suitably employed for the oligomerization process which solvents are defined below.

Suitable simple divalent nickel salts include inorganic as well as organic divalent nickel salts. Illustrative inorganic nickel salts are nickel halides such as nickel chloride, nickel bromide and nickel iodide, nickel carbonate, nickel chlorate, nickel ferrocyanide, and nickel nitrate. Illustrative organic divalent nickel salts are nickel salts of carboxylic acids such as nickel alkanoates of up to ten carbon atoms, preferably of up to six carbon atoms, e.g. nickel formate, nickel acetate, nickel propionate, nickel hexanoate and the like; nickel oxalate; nickel benzoate and nickel naphthenate. Other suitable organic salts include nickel benzenesulfonate, nickel citrate, nickel dimethylglyoxime and nickel acetylacetonate.

Nickel halides, especially nickel chloride, and nickel alkanoates, in part because of their availability at low cost and solubility in polar organic solvents are preferred nickel salts.

Dihydrocarbylphosphinobenzoic Acid:

The o-dihydro-carbylphosphino-benzoate ligands employed in the preparation of the catalyst composition of the invention generally have from eight to 30 carbon atoms, but preferably from 14 to 20 carbon atoms, and are preferably represented by the formula (I):

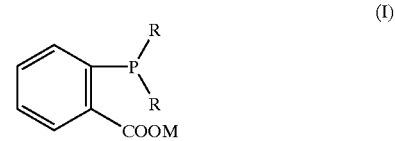

(I)

wherein R is a monovalent hydrocarbyl group and M is hydrogen or an alkali metal. The M group is preferably hydrogen, sodium or potassium. Illustrative examples of R groups are hydrocarbon alkyl groups such as methyl, ethyl, isobutyl, lauryl, stearyl, cyclohexyl, and cyclopentyl; hydrocarbon alkenyl R groups having aromatic substituents such as benzyl, phenylcyclohexyl, and phenylbutenyl. Aromatic R groups such as phenyl, tolyl, xylyl and p-ethylphenyl. Preferred R groups are aromatic groups of six to ten carbon atoms, especially phenyl, and cycloalkyl of five to ten carbon atoms, especially cyclohexyl.

Illustrative examples of o-dihydrocarbyl-phosphinobenzoate ligands of formula (I) are o-diphenylphosphinobenzoic acid, o-(methylphenylphosphino)benzoic acid, o-(ethyltolylphosphino)benzoic acid, o-dicyclohexylphosphinobenzoic acid, o-(cyclohexylphenylphosphino)benzoic acid, o-dipentylphosphinobenzoic acid and the alkali metal salts thereof.

Preferred benzoate ligands of formula (I) are those wherein the R groups are aromatic or cycloalkyl of six to ten carbon atoms, particularly diarylphosphinobenzoic acids, arylcycloalkylphosphinobenzoic acids and the alkali metal salts thereof. Such aryl- and cycloalkyl-substituted phosphino-benzoate ligands are preferred largely because catalyst compositions prepared therefrom catalyze the oligomerization of ethylene to a product mixture containing a high proportion of oligomers in the useful $C_{12}$–$C_{20}$ carbon range.

Although the o-dihydrocarbylphosphinobenzoate ligands are suitably employed as the free acid, better results are occasionally obtained with the alkali metal salts of the o-dihydrocarbylbenzoic acid. The alkali metal salts are suitably preformed from the benzoic acid by treatment with an alkali metal hydroxide or oxide solution prior to catalyst preparation or, alternatively, the carboxylic acid salt is generated in situ by the reaction of equimolar amounts of the carboxylic acid and an alkali metal hydroxide during catalyst preparation.

When preparing the catalyst, the molar ratio of nickel salt to benzoate ligand (free acid or salt thereof) is at least 1:1, i.e., at least one mole nickel salt is provided for each mole of benzoate ligand. Suitable molar ratios of nickel salt to benzoic acid ligand (or salt thereof) range from about 1:1 to about 10:1, although molar ratios of about 1:1 to about 3:1 are preferred.

Boron Hydride Reducing Agent:

In general, any boron hydride salt reducing agent of reasonable purity is suitable for use in the process of the invention. Specific examples include alkali metal borohydrides such as sodium borohydrides, potassium borohydride and lithium borohydride; alkali metal alkoxyborohydrides wherein each alkoxy has one to four carbon atoms, such as sodium trimethoxyborohydride and potassium tripropoxyborohydride and tetraalkylammonium borohydrides wherein each alkyl has one to four carbon atoms, such as tetraethylammonium borohydride. Largely because of commercial availability, alkali metal borohydrides are preferred and especially preferred is sodium borohydride.

When preparing the catalyst, the molar ratio of boron hydride salt to nickel salt is at least about 0.2:1. There does not appear to be a definite upper limit on the boron hydride/nickel ratio, but for economic reasons it is especially preferred that the molar ratio be not greater than about 15:1. The preferred molar ratio of boron hydride to nickel salt is usually between about 0.25:1 and about 5:1; more preferred is a ratio between about 0.5:1 and about 2:1. Best results are often obtained when the molar ratio is about 2:1.

Water Soluble Base:

Any water soluble base may be used for pH adjustment purposes. Examples include potassium bicarbonate, potassium methoxide, potassium ethoxide, potassium isopropoxide, potassium hydroxide, and potassium tert-butoxide as well as the corresponding sodium compounds.

When preparing the catalyst, the molar ratio of water soluble base to boron hydride salt ranges from about 0:1 to about 5:1. The preferred molar ratio of water soluble base to boron hydride is usually between about 0.25:1 and about 2:1.

Phosphite:

Any trivalent phosphite can be used, however, alkyl phosphites are preferred and linear alkyl phosphites are most preferred. Examples of suitable phosphites are triisopropyl-, triisobutyl-, tri-sec-butyl-, trimethyl-, triethyl-, tri-n-propyl-, and tri-n-butylphosphite. When preparing the catalyst, the molar ratio of benzoate ligand to phosphite can range from about 50:1 to about 1000:1, preferably in the range of from about 100:1 to about 300:1.

Catalyst Preparation:

The catalyst composition of the present invention is suitably preformed by contacting the catalyst precursors, i.e., the nickel salt, the benzoic acid ligand, the phosphite, the water soluble base and the boron hydride reducing agent, in the presence of ethylene in a polar organic solvent (or diluent), e.g., polar organic diluents or solvents employed for the oligomerization process which are not reduced by the boron hydride reducing agent. In a preferred modification, the nickel salt, borohydride and base are contacted under an ethylene atmosphere. The benzoic acid ligand and the trivalent phosphite are then added. Generally, the catalyst precursors are contacted under about 10 to about 1,500 psig of ethylene.

The catalyst is generally prepared at temperatures of about 0° C. to about 50° C., although substantially ambient temperatures, e.g. about 10° C. to about 30° C., are preferred. Contact times of about 5 minutes to 1 hour are generally satisfactory, but can be longer.

Reaction Conditions:

The ethylene is contacted with the catalyst composition in the liquid phase in the presence of a reaction solvent or diluent or solvent of up to about 30 liters per mole of ethylene are satisfactorily employed. Generally, the concentration of the catalyst, calculated as nickel metal, in the solvent or diluent is at least 0.001M, but preferably from about 0.002M to about 0.01M.

Suitable solvents (or diluents) are polar organic compounds such as organic compounds containing atoms such as oxygen, sulfur, nitrogen and phosphorus incorporated in functional groups such as, for example, hydroxy, alkoxy, aryloxy, carbalkoxy, alkanoyloxy, cyano, amino, alkylamino, diakylamine, amide, N-alkylamide, N,N-dialkylamide, sulfonylalkyl and like functional groups. Illustrative oxygenated organic solvents are fully esterified polyacyl esters of polyhydroxy alkanes such as glycerol triacetate, tetracyl esters of erythritol, diethylene glycol diacetate; monoesters such as ethyl acetate, butyl propionate and phenyl acetate; cycloalkyl ethers, e.g., dioxane, tetrahydropyran; acyclic alkyl ethers, e.g., dimethoxyethane, diethylene glycol dimethyl ether and dibutyl ether, aromatic ethers such as anisole, 1,4-dimethoxybenzene and p-methoxytoluene; aliphatic alcohols such as methanol trifluoroethanol, hexafluoroethanol, trifluoropropanol, sec-butanol, perfluorobutanol, octanol, dodecanol, cycloalkanols, e.g., cyclopentanol, and cyclo-hexanol, polyhydric acyclic hydroxyalkanes such as glycerol and trimethylene glycol, alkanediols of two to ten carbon atoms such as ethylene glycol, propylene glycol, 1,4-butanediol and 2,5-hexanediol; phenols, such as cresol, p-chlorophenol, m-bromophenol, 2,6-dimethylphenol, p-methoxyphenol, 2,4-dichlorophenol; and alkylene carbonates such as ethylene carbonate, propylene carbonate and butylene carbonate. Illustrative examples of nitrogen-containing organic solvents are nitriles, e.g., acetonitrile and propionitrile; amines, e.g., butylamine, dibutylamine, trihexylamine, N-methylpyrolidine, N-methylpiperidine, and aniline; N,N-dialkylamides, e.g., N,N-dimethylformamide and N,N-dimethylacetamide. Illustrative examples of sulfur-containing solvents are sulfolane and dimethylsulfoxide and illustrative phosphorus-containing solvents are trialkylphosphate, e.g., trimethylphosphate, triethylphosphate and tributylphosphate and hexaalkylphosphoramides such as hexamethylphosphoramide.

Preferred reaction diluents and solvents are oxygenated organic solvents. Especially preferred are alkanediols of four to six carbon atoms, e.g., 1,4butanediol and 2,5-hexanediol. Polar organic solvents and diluents are preferred for use in the process in part because the ethylene oligomerization product mixture is essentially insoluble in such solvents and diluents. For example, when a polar organic solvent such as an alkanediol is employed, a two phase reaction mixture is formed, i.e., one phase comprising the ethylene oligomerization product mixture, i.e., the alpha-olefins, and a second phase comprising the nickel catalyst and the reaction diluent of solvent. Where a two phase reaction is formed, the ethylene oligomerization product phase is separated and the catalyst containing diluent or solvent phase is utilized for further ethylene oligomerization. Polar organic solvents are also preferred in part because the same solvents are employed in catalyst preparation as defined above.

The precise method of establishing ethylene/catalyst contact during the oligomerization reaction is not critical. In one embodiment, the catalyst composition and the solvent are charged to an autoclave or similar pressure reactor, the ethylene is introduced, and the reaction mixture is maintained with agitation at reaction temperature and pressure for the desired reaction period. In the modification wherein a polar organic solvent is employed and a two phase reaction is formed, ethylene is passed in a continuous manner into a reaction zone containing the catalyst composition and the diluent while ethylene oligomerization product mixture which is produced is concomitantly withdrawn from the reaction zone.

In general, the oligomerization process is conducted at moderate temperatures and pressures. Suitable reaction temperatures vary from about 0° C. to about 200° C. The reaction is conducted at or above atmosphere pressure. The precise pressure is not critical so long as the reaction mixture is maintained substantially in a liquid phase. Typical pressures can vary from about 10 psig to about 5,000 psig with the range from about 400 psig to about 1,500 psig being preferred.

The oligomerization products are separated and recovered from the reaction mixture by conventional methods such as fractional distillation, selective extraction, adsorption and the like. The reaction solvent, catalyst and any unreacted ethylene can be recycled for further utilization. Spent catalyst, i.e., catalyst no longer active for ethylene oligomerization, can be regenerated for example, by reacting with additional boron hydride reducing agent and nickel salt in the molar ratios (based on benzoic acid ligand) hereinbefore defined. Additional benzoic acid ligand can be added to the regenerated catalyst but it is not required to regenerate the spent catalyst.

During the oligomerization process ethylene is converted to dimer, trimer, tetramer, and larger oligomers. The products are characterized by a high proportion (greater than about 95%) of linear terminal olefins with high linearity (greater than about 90%). The particular product composition generally depends upon the catalyst of the invention employed, the solvent employed, the reaction conditions, particularly reaction temperatures and diluent and whether the catalyst is used in the homogeneous or heterogeneous state. Depending upon the desired product mixture, the optimized components and conditions can readily be determined by one skilled in the art.

The ethylene oligomer products are materials of established utility and many are chemicals of commerce. The products can be converted by conventional catalysts to the corresponding alcohols.

The instant invention will be illustrated by the following illustrative embodiments which are provided for illustration only and are not to be construed as limiting the invention.

A series of ethylene oligomerization reactions was conducted with a nickel catalyst prepared by reacting nickel chloride hexahydrate ($NiCl_2 \cdot 6H_2O$), potassium hydroxide, a dihydrocarbylphosphinobenzoic acid, sodium borohydride and optionally triethylphosphite in a reaction medium of 1,4-butanediol and ethylene. In this set of examples, Example 1 illustrates the effect of triethylphosphite addition in conjunction with reducing the o-dihydrocarbylphosphinobenzoic charge. Example 2 illustrates the effect of reducing the o-dihydrocarbylphosphinobenzoic charge only. Example 3 represents the normal mode of operation and serves as the control experiment.

EXAMPLE 1

This reaction was conducted by charging 0.496 millimoles of nickel chloride hexahydrate, $NiCl_2 \cdot 6H_2O$, 181 ml 1,4-butanediol and 600 psig of ethylene to a 1-liter reactor at room temperature, with stirring. After approximately 10 minutes of stirring, 0.657 millimoles of sodium borohydride in aqueous solution with 0.225 millimoles of potassium hydroxide were slowly charged to the reactor. A 15 ml portion of 1,4-butanediol was used to flush this solution into the reactor. After an additional 10 minutes of stirring, 4 g of 1,4-butanediol containing 0.188 millimoles of o-dihydrocarbyl-phosphinobenzoic acid and 0.00069 millimoles of triethylphosphite were added to the reactor. An additional 15 ml of 1,4-butanediol was used to flush this solution into the reactor. The reactor pressure was increased to 800 psig of ethylene and the internal temperature was raised to 93° C. Once the temperature stabilized, the ethylene pressure was increased to 1300 psig, with ethylene fed on demand to maintain the operating pressure. The reaction was allowed to proceed until 125 g of ethylene had been consumed. At this point, the reactor was cooled to 65° C. and the ethylene was vented off. The resulting oligomer product was isolated and analyzed for carbon-number distribution (K-factor determination) and alpha olefin content.

EXAMPLE 2

Comparative

The procedure given in Example 1 was followed with the exception that the triethylphosphite was omitted.

EXAMPLE 3

Comparative

The procedure given in Example 1 was followed with the exceptions that triethylphosphite was omitted and the o-dihydrocarbylphosphinobenzoic acid charge was increased to 0.225 millimoles.

The preceding examples were evaluated on the basis of rate, product distribution (K-factor), and product quality. Table 1 contains the rate and K-factor data.

Since Example 3 is the control, its rate has been normalized to 1 with the other rates given in relative terms. Table 2 contains the product quality expressed as weight percent linear alpha olefin for selected carbon numbers.

TABLE 1

Rate and K-factor data.

| Example | Relative Rate | K-Factor |
|---------|---------------|----------|
| 1 | 1.3 | 0.728 |
| 2 | 0.65 | 0.747 |
| 3 | 1.0 | 0.735 |

TABLE 2

Weight percent linear alpha olefin content by carbon number.

| Carbon Number | Example 1 | Example 2 | Example 3 |
|---|---|---|---|
| 10 | 98.2 | 97.7 | 97.8 |
| 12 | 97.8 | 98.2 | 97.2 |
| 14 | 96.3 | 98.3 | 96.6 |
| 16 | 95.6 | 97.6 | 95.7 |
| 18 | 96.3 | 96.9 | 94.9 |

We claim:

1. A catalyst composition comprising the product produced by reacting in a polar organic solvent in the presence of ethylene:
   a) a simple divalent nickel salt having a solubility of at least 0.001 mole per liter in said polar organic solvent;
   b) a boron hydride reducing agent;
   c) a water soluble base;
   d) a ligand selected from the group consisting of o-dihydrocarbylphosphinobenzoic acids and alkali metal salts thereof; and
   e) a trivalent phosphite, wherein the molar ratio of the ligand to the trivalent phosphite ranges from about 50:1 to about 1000:1.

2. The catalyst composition of claim 1 in which the nickel salt comprises a nickel halide.

3. The catalyst composition of claim 1 in which the nickel salt comprises a nickel alkanoate.

4. The catalyst composition of claim 1 in which the boron hydride reducing agent is an alkali metal borohydride.

5. The catalyst composition of claim 1 in which the water soluble base is selected from the group consisting of potassium bicarbonate, potassium methoxide, potassium ethoxide, potassium isopropoxide, potassium hydroxide, potassium tert-butoxide, sodium bicarbonate, sodium methoxide, sodium ethoxide, sodium isopropoxide, sodium hydroxide and sodium tert-butoxide.

6. The catalyst composition of claim 1 in which the water soluble base is potassium hydroxide.

7. The catalyst composition of claim 1 in which the trivalent phosphite is an alkyl phosphite.

8. The catalyst composition of claim 1 in which the trivalent phosphite is triethyl phosphite.

9. The catalyst composition of claim 1 in which the ligand is selected from the group consisting of diarylphosphinobenzoic acids, arylcycloalkyl-phosphinobenzoic acids and the alkali metal salts thereof.

10. The catalyst composition of claim 1 in which the nickel salt comprises a nickel halide, the boron hydride reducing agent is an alkali metal borohydride, the water soluble base is potassium hydroxide, the trivalent phosphite is triethyl phosphite and the ligand is an o-dihydrocarbylphosphinobenzoic acid.

11. A process for preparing a catalyst composition which process comprises:
   contacting in a polar organic solvent in the presence of ethylene:
   a) a simple divalent nickel salt having a solubility of at least 0.001 mole per liter in said polar organic solvent;
   b) a boron hydride reducing agent;
   c) a water soluble base;
   d) a ligand selected from the group consisting of o-dihydrocarbylphosphinobenzoic acids and alkali metal salts thereof; and
   e) a trivalent phosphite, wherein the molar ratio of the ligand to the trivalent phosphite ranges from about 50:1 to 1000:1.

12. The process of claim 11 in which the process is carried out at a temperature of between about 0° and about 200° C.

13. The process of claim 11 in which the nickel salt comprises a nickel halide.

14. The process of claim 11 in which the nickel salt comprises a nickel alkanoate.

15. The process of claim 11 in which the boron hydride reducing agent is an alkali metal borohydride.

16. The process of claim 11 in which the water soluble base is selected from the group consisting of potassium bicarbonate, potassium methoxide, potassium ethoxide, potassium isopropoxide, potassium hydroxide, potassium tert-butoxide, sodium bicarbonate, sodium methoxide, sodium ethoxide, sodium isopropoxide, sodium hydroxide and sodium tert-butoxide.

17. The process of claim 11 in which the water soluble base is potassium hydroxide.

18. The process of claim 11 in which the trivalent phosphite is an alkyl phosphite.

19. The process of claim 11 in which the trivalent phosphite is triethyl phosphite.

20. The process of claim 11 in which the ligand is selected from the group consisting of diarylphosphinobenzoic acids, arylcycloalkylphosphinobenzoic acids and the alkali metal salts thereof.

21. The process of claim 12 in which the nickel salt comprises a nickel halide, the boron hydride reducing agent is an alkali metal borohydride, the water soluble base is potassium hydroxide, the trivalent phosphite is triethyl phosphite and the ligand is an o-dihydrocarbylphosphinobenzoic acid.

22. A process for the preparation of a mixture of olefinic products having high linearity comprising:
   A) contacting ethylene in a polar organic solvent under conditions effective to produce linear, alpha-olefins in the presence of a catalyst produced by reacting components comprising:
   a) a simple divalent nickel salt having a solubility of at least 0.001 mole per liter in said polar organic solvent;
   b) a boron hydride reducing agent;
   c) a water soluble base;
   d) a ligand selected from the group consisting of o-dihydrocarbylphosphinobenzoic acids and alkali metal salts thereof; and,
   e) a trivalent phosphite, wherein the molar ratio of the ligand to the trivalent phosphite ranges from about 50:1 to about 1000:1; thereby producing a mixture of olefinic products having high linearity; and
   B) recovering the olefinic products having high linearity.

23. The process of claim 22 in which the production of the catalyst in A is carried out at a temperature of between about 0° and about 200° C.

24. The process of claim 22 in which the nickel salt comprises a nickel halide.

25. The process of claim 22 in which the nickel salt comprises a nickel alkanoate.

26. The process of claim 22 in which the boron hydride reducing agent is an alkali metal borohydride.

27. The process of claim 22 in which the water soluble base is selected from the group consisting of potassium bicarbonate, potassium methoxide, potassium ethoxide, potassium isopropoxide, potassium hydroxide, potassium tert-butoxide, sodium bicarbonate, sodium methoxide, sodium ethoxide, sodium isopropoxide, sodium hydroxide and sodium tert-butoxide.

28. The process of claim 22 in which the water soluble base is potassium hydroxide.

29. The process of claim 22 in which the trivalent phosphite is an alkyl phosphite.

30. The process of claim 22 in which the trivalent phosphite is triethyl phosphite.

31. The process of claim 22 in which the ligand is selected from the group consisting of diarylphosphinobenzoic acids, arylcycloalkylphosphinobenzoic acids and the alkali metal salts thereof.

32. The process of claim 23 in which the nickel salt comprises a nickel halide, the boron hydride reducing agent is an alkali metal borohydride, the water soluble base is potassium hydroxide, the trivalent phosphite is triethyl phosphite and the ligand is an o-dihydrocarbylphosphinobenzoic acid.

33. The catalyst composition of claim 1 wherein the molar ratio of the ligand to the trivalent phosphite ranges from about 100:1 to about 300:1.

34. The process of claim 11 wherein the molar ratio of the ligand to the trivalent phosphite ranges from about 100:1 to about 300:1.

35. The process of claim 22 wherein the molar ratio of the ligand to the trivalent phosphite ranges from about 100:1 to about 300:1.

* * * * *